(12) United States Patent
Bloch et al.

(10) Patent No.: US 9,289,453 B2
(45) Date of Patent: Mar. 22, 2016

(54) TRANSPLANTATION OF CELLS INTO THE NASAL CAVITY AND THE SUBARACHNOID CRANIAL SPACE

(71) Applicant: Ramot at Tel-Aviv University Ltd., Tel-Aviv (IL)

(72) Inventors: Konstantin Bloch, Petach-Tikva (IL); Pnina Vardi, Haifa (IL); Alexey Vanichkin, Petach-Tikva (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 14 days.

(21) Appl. No.: 13/916,743

(22) Filed: Jun. 13, 2013

(65) Prior Publication Data

US 2013/0336938 A1 Dec. 19, 2013

Related U.S. Application Data

(60) Provisional application No. 61/659,456, filed on Jun. 14, 2012, provisional application No. 61/773,263, filed on Mar. 6, 2013.

(51) Int. Cl.
| | |
|---|---|
| *A01N 63/00* | (2006.01) |
| *A01N 65/00* | (2009.01) |
| *A61B 1/00* | (2006.01) |
| *A61K 35/39* | (2015.01) |
| *A61K 45/06* | (2006.01) |
| *A61B 1/233* | (2006.01) |

(52) U.S. Cl.
CPC ............... *A61K 35/39* (2013.01); *A61B 1/233* (2013.01); *A61K 45/06* (2013.01)

(58) Field of Classification Search
CPC ......... A61K 45/06; A61K 35/39; A61B 1/233
USPC ........................................... 424/93.21
See application file for complete search history.

(56) References Cited

U.S. PATENT DOCUMENTS 5,869,077 A * 2/1999 Dionne et al. .............. 424/422
2013/0336938 A1 12/2013 Bloch et al.

OTHER PUBLICATIONS

Park et al., 2010, J. Craniofacial Srgery. 21: 557-560.*
Tze-b et al., 1984, Transplantation. 38: 107-111 Abstract p. 1/1.*
Tze et al., 1988, Diabetes. 37: 383-392.*
Sauerbier et al., 2010, Tissue Eng. Part C Methods. 16: 1033-1039; Abstract p. 1/1.*
Habisch et al 2007, J.Neural.Transm. 114:1395-406.*
Firouzi et al. "Transplantation of Schwann Cells to Subarachnoid Space Induces Repair in Contused Rat Spinal Cord", Neuroscience Letters, 402: 66-70, 2006.

* cited by examiner

*Primary Examiner* — Scott Long
*Assistant Examiner* — Kelaginamane T Hiriyanna

(57) ABSTRACT

A method of transplanting cells into a subject is disclosed. The method comprises transplanting the cells into the paranasal sinus of the subject or the subarachnoid cavity situated between the frontal bone of skull and the olfactory bulb of the subject. Devices for paranasal sinus transplantation and subarachnoid cavity transplantation are also disclosed.

11 Claims, 11 Drawing Sheets
(6 of 11 Drawing Sheet(s) Filed in Color)

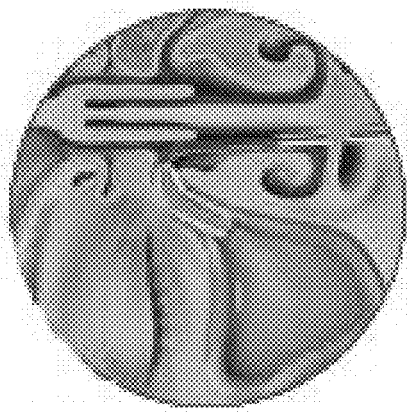
FIG. 1C Maxillary
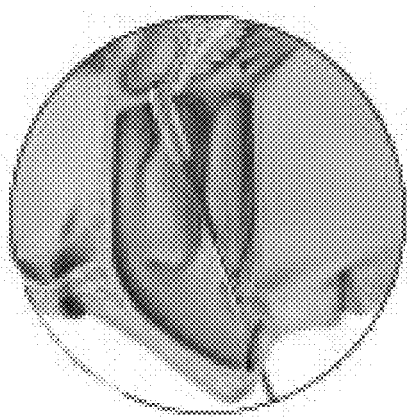
FIG. 1B Sphenoid
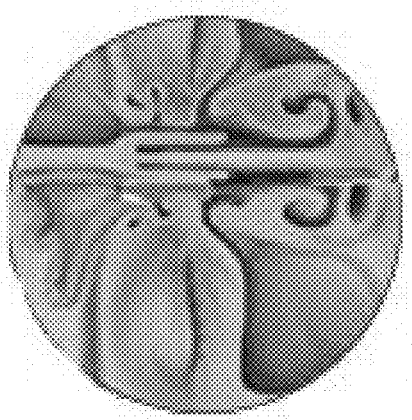
FIG. 1A Frontal

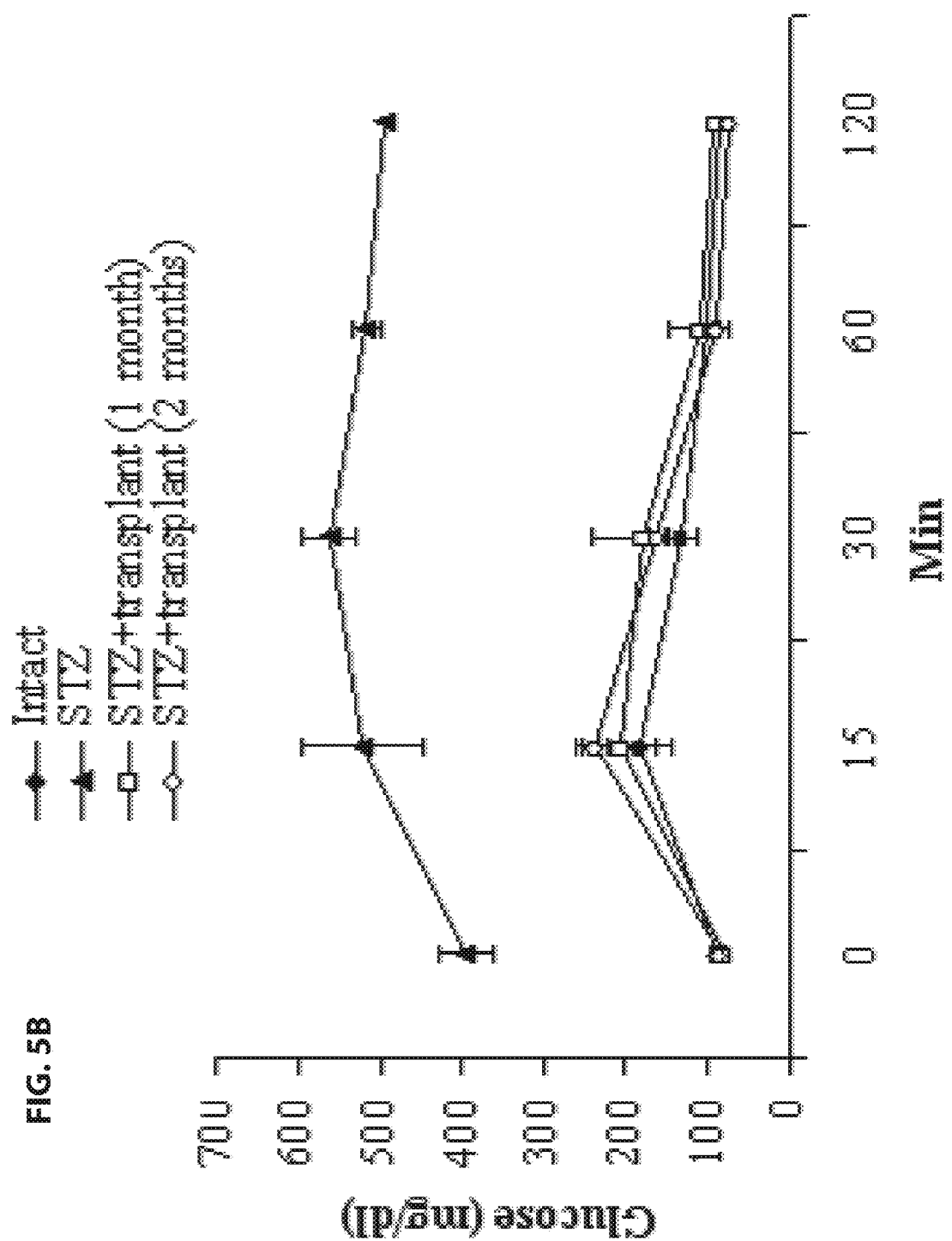

TRANSPLANTATION OF CELLS INTO THE NASAL CAVITY AND THE SUBARACHNOID CRANIAL SPACE

RELATED APPLICATIONS

This application claims the benefit of priority under 35 USC 119(e) of U.S. Provisional Patent Application Nos. 61/659,456 filed Jun. 14, 2012 and 61/773,263 filed Mar. 6, 2013. The contents of all of the above applications are incorporated by reference as if fully set forth herein.

FIELD AND BACKGROUND OF THE INVENTION

The present invention, in some embodiments thereof, relates to a method of transplanting cells into the nasal cavity and, more particularly, but not exclusively, into the paranasal sinuses (PNS), and into the subarachnoid cavity.

Cell therapy is one of the most promising future techniques in the medical arsenal for the repair of damaged or destroyed tissue and/or for the replacement of dysfunctional cells. The diseases which cell therapy can target are very varied: Hormonal dysfunction, such as diabetes and growth hormone deficiency; neurodegenerative diseases, such as Parkinson's, Alzheimer's and Huntington's; and cardiovascular lesions, such as myocardial infarction, peripheral vascular ischaemia; as well as lesions in the cornea, skeletal muscle, skin, joints and bones etc. The objective of cell therapy is to restore the lost function rather than produce a new organ, which could cause duplicity and undesirable effects. Several resources of cells can be used to restore the damaged tissue, such as donor cells from human cadavers, resident stem cells, multipotent adult progenitor cells or embryonic stem cells.

Type 1 Diabetes Mellitus (T1DM) as well as Type 2 (T2DM) are both diseases resulting from pancreatic islets dysfunction and insulin dependency. Islet transplantation is a potential successful treatment for T1DM patients and a subgroup of patients with T2DM. Currently, clinical trials in humans such as the "Edmonton protocol" show that long-term outcomes of islet transplantation into the liver are hampered by a gradual decrease in islet function occurring during the early post transplantation period. The dramatic initial loss of islets is believed to be related to hypoxia at the transplantation site. In addition, the liver site requires an immunosuppressive therapy and is associated with procedure-related complications, including haemorrhage and thrombosis. The spleen, eye, brain, thymus, testes, pancreas, kidney capsule, peritoneum, bone morrow, lung, subcutis, muscle and omental pouch have been explored as potential sites for islet transplantation. Currently, experimental islet transplantations in these sites are hampered by insufficient oxygenation, immune rejection, limited space and complicated surgical procedure (Shapiro A J et al, Curr Diab Rep. 2011; 11(5):345-54; Merani et al., Br J Surg. 2008; 95(12):1449-61).

Firouzi M et al., Neurosci Lett. 2006 Jul. 10; 402(1-2):66-70, teaches transplantation of Schwann cells into the subarachnoid cavity.

SUMMARY OF THE INVENTION

According to an aspect of some embodiments of the present invention there is provided a method of transplanting cells into a subject in need thereof comprising transplanting the cells into the paranasal sinus of the subject or the subarachnoid cavity situated between the frontal bone of the skull and the olfactory bulb of the subject, thereby transplanting the cells.

According to an aspect of some embodiments of the present invention there is provided a method of treating a disease in a subject in need thereof, comprising transplanting a therapeutically effective amount of cells into the paranasal sinus of the subject or the subarachnoid cavity situated between the frontal bone of the skull and the olfactory bulb of the subject, thereby treating the disease.

According to an aspect of some embodiments of the present invention there is provided a method of treating a disease in a subject in need thereof, comprising administering a therapeutically effective amount of cell aggregates into the nasal cavity of the subject or the subarachnoid cavity situated between the frontal bone of skull and the olfactory bulb of the subject, wherein said cell aggregates are greater than 50 microns in diameter, thereby treating the disease.

According to an aspect of some embodiments of the present invention there is provided an endoscopic device comprising a container attached to a flexible tubing and an optic fiber, wherein the inner surface of the container is coated with an agent that prevents adhesiveness of cell aggregates thereto.

According to some embodiments of the invention, when the disease is Diabetes, the cell aggregates comprises islets.

According to some embodiments of the invention, the disease is an autoimmune disease.

According to some embodiments of the invention, the disease is selected from the group consisting of a hormone deficiency disease, a clotting factor disorder, a brain disorder and an enzyme deficiency disease.

According to some embodiments of the invention, the autoimmune disease is selected from the group consisting of Diabetes, Hashimotos throiditis and Addison disease.

According to some embodiments of the invention, the hormone of the hormone deficiency disease is selected from the group consisting of insulin, thyroxine, growth hormone, testosterone, oestrogen, erythropoietin and aldosterone.

According to some embodiments of the invention, the enzyme of the enzyme deficiency disease is selected from the group consisting of lysosomal enzyme is selected from the group consisting of glucocerebrosidase (GCD), acid sphingomyelinase, hexosaminidase, α-N-acetylgalactosaminidise, acid lipase, α-galactosidase, α-L-iduronidase, iduronate sulfatase, α-mannosidase, sialidase, α fucosidase, $G_{M1}$-β-galctosidase, ceramide lactosidase, arylsulfatase A, β galactosidase and ceramidase.

According to some embodiments of the invention, the clotting factor disease is hemophilia A.

According to some embodiments of the invention, the brain disorder is a neurodegenerative disorder.

According to some embodiments of the invention, the cells comprise genetically modified cells.

According to some embodiments of the invention, the cells express a recombinant polypeptide.

According to some embodiments of the invention, the cells are seeded on a scaffold prior to the transplanting.

According to some embodiments of the invention, the method further comprises inserting a scaffold into the paranasal sinus or the subarachnoid cavity prior to the transplanting.

According to some embodiments of the invention, the cells comprise stem cells.

According to some embodiments of the invention, the cells comprise immunoisolated cells.

According to some embodiments of the invention, the cells comprise pancreatic beta cells.

According to some embodiments of the invention, the cells are autologous to the subject.

According to some embodiments of the invention, the cells are non-autologous to the subject.

According to some embodiments of the invention, the paranasal sinuses are selected from the group consisting of the maxillary sinuses, frontal sinuses, ethmoid sinuses, and the sphenoid sinuses.

According to some embodiments of the invention, the method further comprises administering to the subject an immunosuppressive agent.

According to some embodiments of the invention, the transplanting is effected by endoscopy.

According to some embodiments of the invention, the cell aggregates comprise pancreatic islets.

According to some embodiments of the invention, the inner diameter of the tubing is between about 200 µm-1000 µm.

According to some embodiments of the invention, the container comprises a population of cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawings will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-C are a pictorial illustration of the position of the paranasal sinuses and nasal path for non-invasive cell delivery into different sinuses.

Figure 2:
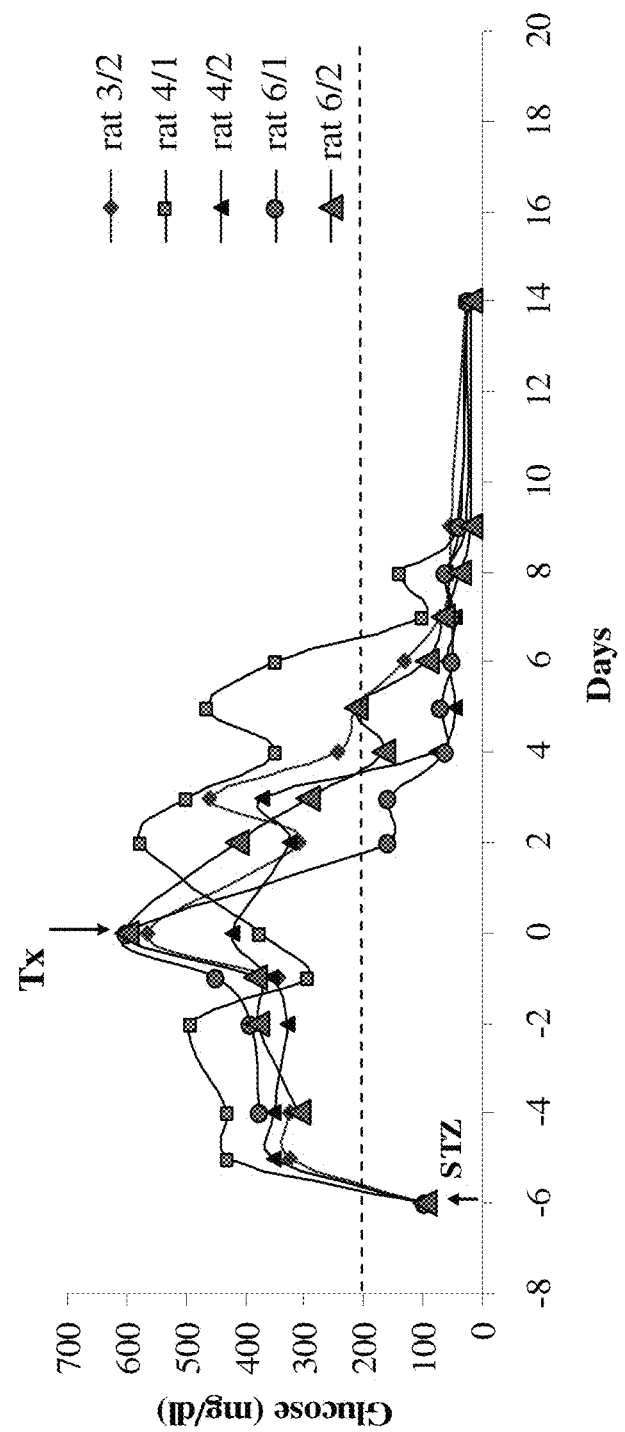

FIG. 2 is a graph illustrating the hypoglycemic effect of insulinoma INS-1 cell transplanted into the paranasal sinus (PNS) of streptozotocin (STZ)-diabetic rats. Diabetes was induced in 5 male Lewis rats by i.v. injection of 85 mg STZ/kg. Rats were pretreated with 10 mg/kg CyA 2 days prior to transplantation followed by a daily dosage of CyA. One week after STZ injection, about $30 \times 10^6$ cells were implanted (Tx) in PNS of diabetic rats. Head was removed for immunohistochemical analysis two weeks following cell implantation.

Figure 3A:
Figure 3B:

FIGS. 3A-B are photographs photograph of a PNS implantation site under low (FIG. 3A) and high (FIG. 3B) magnifications. Immunoperoxidase insulin staining (brown color) of rat insulinoma cells INS-1 implanted in PNS.

Figure 4:
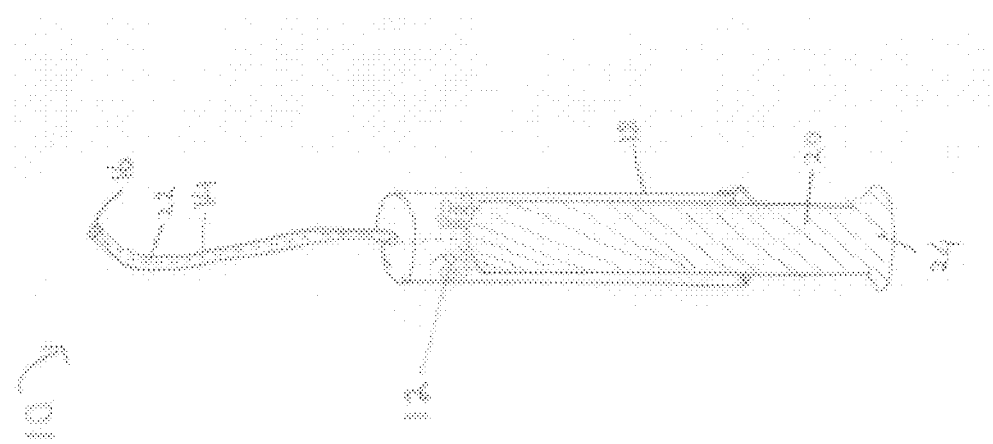

FIG. 4 is a diagram of an exemplary device which can be used to transplant the cells into the nasal and/or paranasal cavity of a subject.

FIGS. 5A-D illustrate long-term glucose metabolism after islet transplantation in subarachnoid cavity of diabetic rats. A. Non fasting blood glucose profile. Glucose concentrations in a group of non transplanted STZ-diabetic animals were more than 350 mg/dl for the experimental period. B. Intraperitoneal test tolerance to glucose (IPTTG). IPTTG was performed by injecting glucose at a concentration of 1 g/kg body weight following 6 h fast. Blood glucose was monitored by sampling from the tail vein periodically up to 120 min as indicated. The data represent the mean±SD of five independent rats in a group of intact animals (Intact) and in a group of non transplanted STZ-diabetic animals (STZ) and three rats in a group of transplanted STZ-diabetic animals (STZ+transplant). Arrows show the time of STZ-treatment and islet transplantation (Tr). C. Immunohistochemical image of islets transplanted in the subarachnoid cavity of rats treated with STZ: peroxidase staining of insulin (brown). D. Immunofluorescent double staining of islets transplanted in the subarachnoid cavity of rats treated with STZ (insulin in red, glucagon in green). Tissues for histological analysis were taken two months after transplantation. Scale bars—200 µm.

Figure 6:
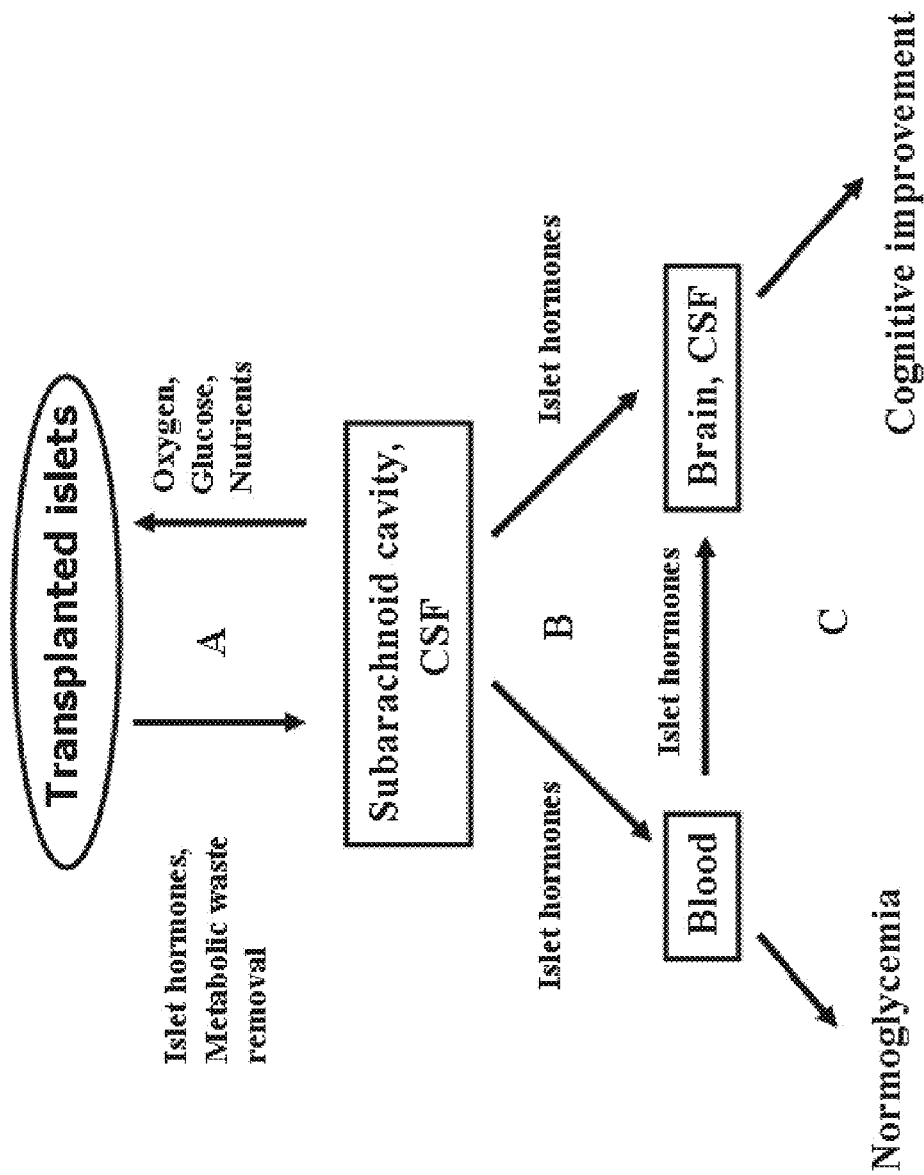

FIG. 6 Schematic presentation of possible anti-diabetic and anti-dementia effects of islets transplanted in subarachnoid cavity. A. The arrows show pathways for the oxygen, glucose and nutrition supply to the transplanted islets from surrounding tissues and the CSF, as well as hormone delivery and metabolic waste removal from grafted islets. B. The role of subarachnoid cavity/CSF in facilitating islet hormone transport into the blood and direct hormone delivery into the brain. C. Effects on glucose homeostasis and cognitive functions.

Figure 7A:
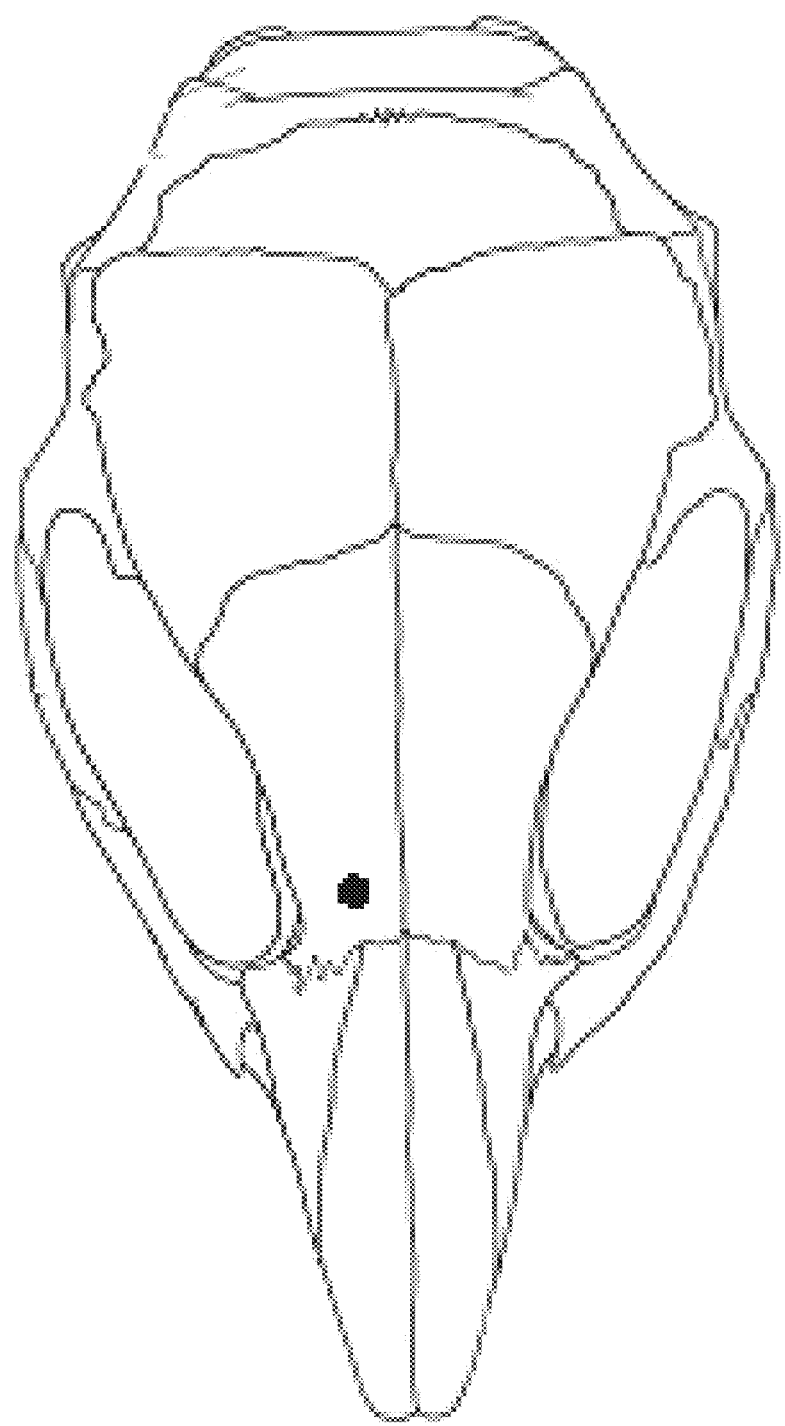
Figure 7B:
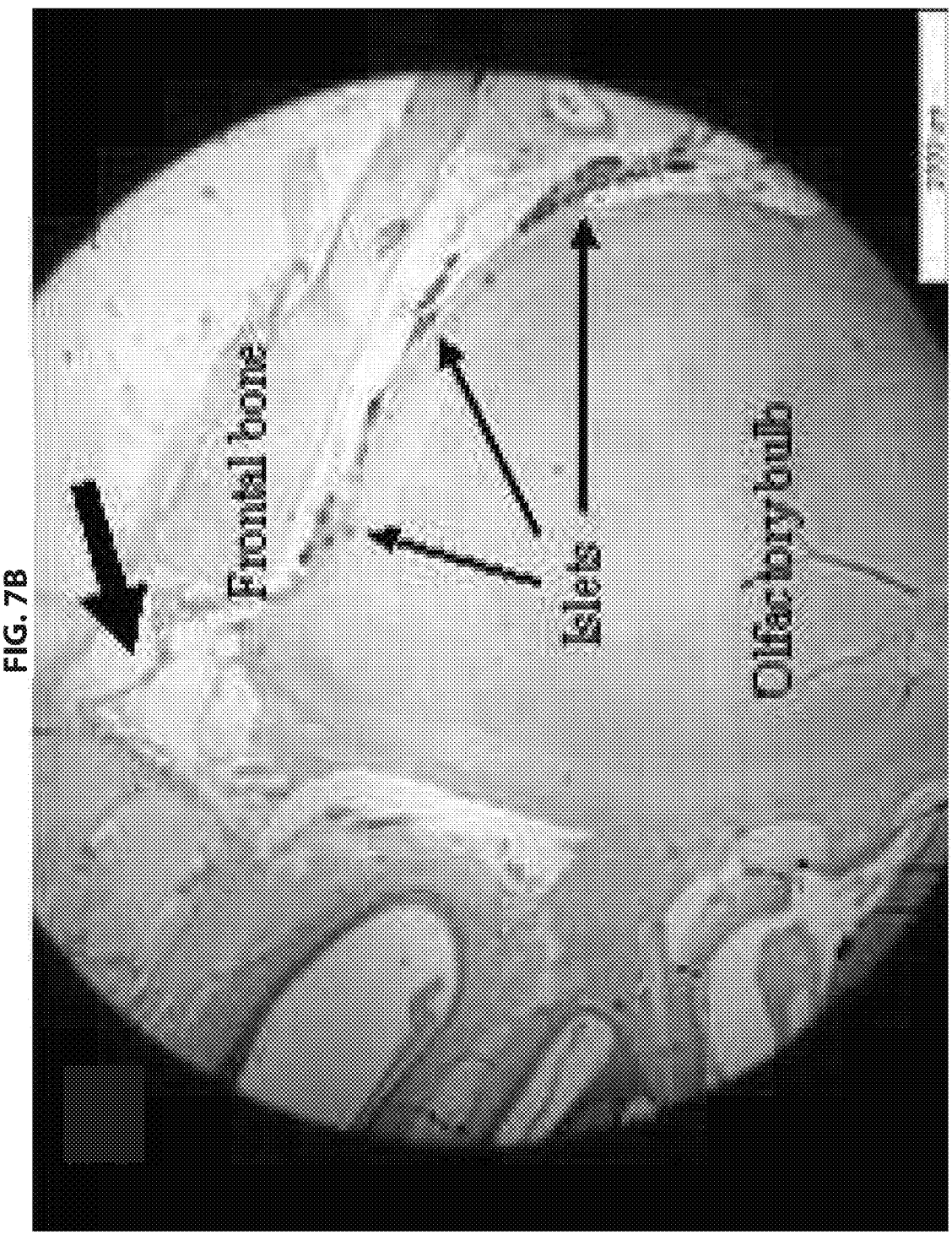

FIGS. 7A-B. Burr hole position in rat skull. A. Schematic presentation (black circle indicates position of burr hole in the frontal bone of the skull). B. Microscopy image of a rat skull with position of burr hole (bold arrow) and transplanted islets stained for insulin. Scale bar—2000 µm.

DESCRIPTION OF SPECIFIC EMBODIMENTS OF THE INVENTION

The present invention, in some embodiments thereof, relates to a method of transplanting cells and, more particularly, but not exclusively, into the paranasal sinuses or the subarachnoid cavity situated between the frontal bone of the skull and the olfactory bulb of the subject.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Various sites have been explored for the transplantation of pancreatic islets including the spleen, eye, brain, thymus, testes, pancreas, kidney capsule, peritoneum, bone morrow, lung, subcutis, muscle and omental pouch. Currently, experimental islet transplantations in these sites are hampered by insufficient oxygenation, immune rejection, limited space and complicated surgical procedures.

The present inventors propose two new sites for transplantation, namely the highly oxygenated air-filled paranasal sinuses and the subarachnoid cavity situated between the frontal bone of the skull and the olfactory bulb.

Human paranasal sinuses are composed of a group of four paired air-filled spaces surrounding the nasal cavity (maxillary sinuses), above the eyes (frontal sinuses), between the eyes (ethmoid sinuses), and behind the ethmoids (sphenoid sinuses).

When compared to the currently tested alternative sites for islet transplantations, the paranasal sinuses have important advantages:

1. Easy access, allowing for a noninvasive or minimally invasive procedure of cell implantation in humans;
2. Excellent physiological oxygenation due to continuous aeration during respiration (pO2=96 mmHg in PNS v.s pO2=5 mmHg in islets transplanted into liver; and
3. Sufficient space in the case of islet transplantation (human PNS volume is ~60-80 cm$^3$; vs. transplanted islets volume of ~1-2 cm$^3$).

Whilst reducing the present invention to practice, the present inventors have shown that STZ-diabetic rats became hypoglycemic during one week following transplantation of insulin producing INS cells into the PNS (FIG. 2).

The olfactory bulb is known to be enriched with insulin receptor, displays the highest transport rate for insulin in the brain and plays an important role in development of different neurodegenerative diseases, particularly in Alzheimer's and Parkinson's diseases. It has been shown that decreased brain insulin levels and/or signaling are associated with impaired learning, memory and various neurodegenerative diseases.

Whilst further reducing the present invention to practice, the present inventors showed that islet cell transplantation at a particular position in the subarachnoid cavity (i.e. situated between the frontal bone of the skull and the olfactory bulb) enabled the assembly of grafted islets directly onto the glomeruli of the olfactory bulb. As illustrated in FIGS. 5A-D, severely diabetic rats which were transplanted with islets at this site became normoglycemic after two days and demonstrated normal glucose tolerance typical for healthy animals.

Thus, according to one aspect of the present invention, there is provided a method of transplanting cells into a subject in need thereof comprising transplanting the cells into the nasal cavity of the subject or the subarachnoid cavity situated between the frontal bone of the skull and the olfactory bulb, thereby transplanting the cells.

Nasal Cavity:

The phrase "nasal cavity" refers to air filled space above and behind the nose in the middle of the face including the paranasal sinuses. According to one embodiment, the administration is effected through the nose (e.g. via the nostrils). According to another embodiment, the administration is effected via the mouth.

According to one embodiment, the transplanting is into the paranasal sinus.

According to this aspect of the present invention, the term "transplanting into the paranasal sinus" refers to administration into at least one paranasal sinus of the subject. Preferably, at least about 20%, 30%, 40%, 50%, 60%, 70%, 80%, 90% of the transplanted cells reach the paranasal sinus at least 5 minutes following transplantation.

Preferably, at least about 20%, 30%, 40%, 50%, 60%, 70%, 80%, 90% of the transplanted cells reach the paranasal sinus at least 1 minute following transplantation.

Preferably, at least about 20%, 30%, 40%, 50%, 60%, 70%, 80%, 90% of the transplanted cells reach the paranasal sinus at least 20 seconds following transplantation.

According to one embodiment, the transplanting is local—i.e. the cells enter the cavity directly by the act of transplantation and not by systemic routes, and do not migrate from a different transplantation site outside the paranasal sinus. It will be appreciated that following the transplantation, the cells are capable of migrating out of the transplantation site (paranasal sinus) to act systemically.

According to one embodiment, the transplanting is effected by introduction of the cellular composition into the body using a device (e.g. via endoscopy), wherein at least a portion of the device enters the nose (and more preferably the paranasal cavity of the sinus). Further description of the device is provided herein below.

The paranasal sinuses may be any one of the maxillary sinuses, frontal sinuses, ethmoid sinuses, and the sphenoid sinuses as illustrated in FIGS. 1A-C.

Subarachnoid Cavity:

As used herein, the term "subarachnoid cavity" refers to the space in the meninges beneath the arachnoid membrane and above the pia mater that contains the cerebrospinal fluid.

In order to transplant, into the subarachnoid cavity, preferably the frontal bone is pierced and the dura mater and the arachnoid membrane perforated.

The position of insertion of the transplant should be located such that the cells are capable of diffusing onto the olfactory bulb.

Preferably, at least about 20%, 30%, 40%, 50%, 60%, 70%, 80%, or 90% of the transplanted cells reach the olfactory bulb at least 5 minutes following transplantation.

Preferably, at least about 20%, 30%, 40%, 50%, 60%, 70%, 80%, or 90% of the transplanted cells reach the olfactory bulb at least 1 minute following transplantation.

Preferably, at least about 20%, 30%, 40%, 50%, 60%, 70%, 80%, or 90% of the transplanted cells reach the olfactory bulb at least 20 seconds following transplantation.

According to one embodiment, the transplanting is local—i.e. the cells enter the subarachnoid cavity directly by the act of transplantation and not by systemic routes, and do not migrate from a different transplantation site outside the subarachnoid cavity. It will be appreciated that following the transplantation, the cells are capable of migrating out of the transplantation site (subarachnoid cavity) to act systemically.

The composition is a "transplant", and the mammal is the recipient. The transplant and recipient may be syngeneic, allogenic, or xenogeneic.

The term "cells" as used herein, refers to embryonic, fetal, pediatric, or adult cells or tissues, including but not limited to, stem cells, induced pluripotent stem cells, precursors cells, and progenitor cells.

The cell may be in an isolated form (e.g. in a single cell suspension), may be part of a cell aggregate (e.g. comprised in a pancreatic islet) or may be part of a tissue or organ.

As used herein, the term "cell aggregate" refers to a plurality of cells that are connected by a physical interaction—i.e. a cell cluster. The cell aggregate may comprise 20 cells, 100 cells, 500 cells, 1000 cells, 5000 cells or more. The cell aggregate may comprise more than one type of cell. Thus, for example, an islet comprises alpha cells producing glucagon (15-20% of total islet cells), beta cells producing insulin and amylin (65-80%), delta cells producing somatostatin (3-10%), PP cells producing pancreatic polypeptide (3-5%) and epsilon cells producing ghrelin (<1%).

According to one embodiment, the cell aggregate is between about 50 μm-500 μm, 100 μm-500 μm, 100 μm-300 μm or 200-400 μm in diameter.

The cells may be derived from a primary culture or may be derived from a cell line.

The cells may be fresh, frozen or preserved in any other way known in the art (e.g. cryopreserved).

According to another embodiment, the cells are derived from the pancreas or the liver.

Typically, the cells secrete a factor (e.g. a polypeptide) that is useful for the treatment of a disease.

Such factors include for example, hormones including but not limited to insulin, thyroxine, growth hormone, testosterone, oestrogen, erythropoietin and aldosterone; enzymes, including but not limited to lysosomal enzyme such as glucocerebrosidase (GCD), acid sphingomyelinase, hexosaminidase, α-N-acetylgalactosaminidise, acid lipase, α-galactosidase, α-L-iduronidase, iduronate sulfatase, α-mannosidase, sialidase, α fucosidase, $G_{M1}$-β-galctosidase, ceramide lactosidase, arylsulfatase A, β galactosidase and ceramidase; clotting factors such as factor VIII.

According to a preferred embodiment, the cells secrete pancreatic hormones (e.g. insulin, glucagon, somatostatin).

As used herein, the term "pancreatic hormones" refers to hormones obtained by synthesis or recombination, in which the peptide sequence is the sequence of human hormone, includes the allelic variations and the homologs. The polypeptide sequence of the hormone may be modified to improve the function of the hormone (e.g. long lasting).

Cells which secrete neurotrophic factors are also contemplated by the present invention.

As used herein, the phrase "neurotrophic factor" refers to a cell factor that acts on the cerebral nervous system comprising growth, differentiation, functional maintenance and/or survival effects on neurons. Examples of neurotrophic factors include, but are not limited to, glial derived neurotrophic factor (GDNF), GenBank accession nos. L19063, L15306; brain-derived neurotrophic factor (BDNF), GenBank accession no CAA62632; neurotrophin-3 (NT-3), GenBank Accession No. M37763; neurotrophin-4/5; Neurturin (NTN), GenBank Accession No. NP_004549; Neurotrophin-4, GenBank Accession No. M86528; Persephin, GenBank accession no. AAC39640; brain derived neurotrophic factor, (BDNF), GenBank accession no. CAA42761; artemin (ART), GenBank accession no. AAD13110; ciliary neurotrophic factor (CNTF), GenBank accession no. NP_000605; insulin growth factor-I (IGF-1), GenBank accession no. NP_000609; and Neublastin GenBank accession no. AAD21075.

Cells which secrete neuropeptides are also contemplated by the present invention. Examples of neuropeptides include, but are not limited to Oxytocin, Vasopressin, Corticotropin releasing hormone (CRH), Growth hormone releasing hormone (GHRH), Luteinizing hormone releasing hormone (LHRH), Somatostatin growth hormone release inhibiting hormone, Thyrotropin releasing hormone (TRH), Neurokinin α (substance K), Neurokinin β, Neuropeptide K, Substance P, β-endorphin, Dynorphin, Met- and leu-enkephalin, Neuropeptide tyrosine (NPY), Pancreatic polypeptide, Peptide tyrosine-tyrosine (PYY), Glucogen-like peptide-1 (GLP-1), Peptide histidine isoleucine (PHI), Pituitary adenylate cyclase activating peptide (PACAP), Vasoactive intestinal polypeptide (VIP), Brain natriuretic peptide, Calcitonin gene-related peptide (CGRP) (α- and β-form), Cholecystokinin (CCK), Galanin, Islet amyloid polypeptide (IAPP), Melanin concentrating hormone (MCH), ACTH, α-MSH, Neuropeptide FF, Neurotensin, Parathyroid hormone related protein, Agouti gene-related protein (AGRP), Cocaine and amphetamine regulated transcript (CART)/peptide, Endomorphin-1 and -2, 5-HT-moduline, Hypocretins/orexins Nociceptin/orphanin FQ, Nocistatin, Prolactin releasing peptide, Secretoneurin and Urocortin.

Cells which secrete neurotransmitters are also contemplated by the present invention.

A neurotransmitter according to the teaching of the present invention can be any substances which is released on excitation from the axon terminal of a presynaptic neuron of the central or peripheral nervous system and travel across the synaptic cleft to either excite or inhibit the target cell. The neurotransmitter can be, for example, dopamine, norepinephrine, epinephrine, gamma aminobutyric acid, serotonin, acetylcholine, glycine, histamine, vasopressin, oxytocin, a tachykinin, cholecytokinin (CCK), neuropeptide Y (NPY), neurotensin, somatostatin, an opioid peptide, a purine or glutamic acid.

Examples of diseases that may be treated using the cells described herein include, but are not limited to an autoimmune disease (e.g. Diabetes type I or type II), Hashimotos throiditis and Addison disease, a clotting factor disorder (e.g. Hemophilia), a brain disorder (e.g. neurodegenerative disorders such as Alzheimer's or Parkinson's disease), a disease or disorder associated with under-production of a hormone and an enzyme deficiency disease. Since the cells of the present invention may be selected to secrete a particular hormone, it is contemplated that the cells may also be useful for the treatment of reproductive disorders, contraception or to increase fertility.

Table 1 below provides a list of brain diseases together with the important factor useful for treating the diseases.

TABLE 1

| REF | factors | Disease |
| --- | --- | --- |
| Walker D G, et al. Brain Res 1998; 794: 181-7. | BDNF, FGF, GDNF | Parkinson's |
| Lorigados L, et al. Rev Neurol 1998; 26: 744-8. | | |
| Mogi M, et al. Neurosci Lett 1994; 180: 147-50. | | |
| Howells D W, et al. Exp Neurol 2000; 166: 127-35. | | |
| Beck K D, et al. Nature 1995; 373: 339-41. | | |
| Tomac A, et al. Nature 1995; 373: 335-9. | | |
| Gash D M, et al. Nature 1996; 380: 252-5. | | |
| Choi-Lundberg D L, Science 1997; 275: 838-41. | | |
| Bozzi Y, Borrelli E. Eur J Neurosci 1999; 11: 1275-84. | | |
| Chauhan N B, et al Soc Neurosci Abstr 1998; 24: 1465. | | |
| Chauhan N B, et al, Neurology 1999; 52: A212-213. | | |
| G. W. Mathern, Mol. Chem. Neuropathol. 30 1-2 (1997), pp. 53-76. | BDNF, NT-3, | Epilepsy |
| Lucia Tapia-Arancibia et al. Frontiers in Neuroendocrinology 2004 July; 25(2): 77-107. | | |
| RYUTA KOYAMA and YUJI IKEGAYA; NEUROSCIENCE UPDATE 2005 August; 11(4): 282-7. | | |
| Gerald Seifert, et al., Nature Reviews Neuroscience 7, 194-206 (March 2006). | | |

TABLE 1-continued

| REF | factors | Disease |
| --- | --- | --- |
| Luis H. Et al., Brain Research Reviews 2004 December; 47(1-3): 263-74.<br>Bradley W G. Ann Neurol 1995; 38: 971.<br>Haase G, et al. Nat Med 1997; 3: 429-36.<br>Arakawa Y, J Neurosci 1990; 10: 3507-15. | NT3, IGF1, BDNF, | ALS |
| Ron D, Janak PH. Rev Neurosci. 2005; 16(4): 277-85. | GDNF | Drug and alcohol addiction |
| Crutcher K A, et al. J Neurosci 1993; 6: 2540-50.<br>Scott S A, et al. Nerve growth factor in Alzheimer's disease: increased levels throughout the brain coupled with declines in nucleus basalis. J Neurosci 1995; 15: 6213-21.<br>Peng S, et al. J Neuropathol Exp Neurol 2004; 63: 641-9.<br>Murer M G, et al. Neuroscience 1999; 88: 1015-32. | BDNF | Alzheimer's |
| Martinez-Serrano A, Bjorklund A. Trends Neurosci 1997; 20: 530-8.<br>Perez-Navarro E, et al. J Neurochem 2000; 75: 2190-9.<br>Perez-Navarro E, et al. Neuroscience 1999; 91: 1257-64. | BDNF, NT-3, or NT-4/5 | Huntington's |
| Gal Shoval, Abraham Weizmana; Eur Neuropsychopharmacol. 2005 May; 15(3): 319-29.<br>Levi-Montalcini, R., 1987. Biosci. Rep. 7, 681-699.<br>Hattori, M., Nanko, S., 1995. Biochem. Biophys. Res. Commun. 209, 513-518.<br>Virgos, C., 2001, Schizophr. Res. 49, 65-71. | NT-3, BDNF | Schizophrenia |
| Paul A. Sieving, et al., Proc Natl Acad Sci USA. 2006 Mar. 7; 103(10): 3896-901. | CNTF | Optic nerve |
| Wu D; Neuro Rx. 2005 January; 2(1): 120-8. | FGF, BDNF | Stroke |

It will be appreciated that when the transplantation site is the subarachnoid cavity, insulin producing cells (e.g. pancreatic islet cells) may be used to treat brain disorders such as dementia and other neurodegenerative diseases (for example, those listed herein above) since it is known that adequate insulin supply to the brain restores cerebral glucose homeostasis and cognitive functions.

According to one embodiment, the cells are genetically modified to express a recombinant protein. Preferably, the recombinant protein is secreted from the cell.

Examples of recombinant proteins that may be expressed (and preferably secreted) in the cells of the present invention include, but are not limited to an antibody, insulin, human growth hormone (rHGH), follicle stimulating hormone, factor VIII, erythropoietin, Granulocyte colony-stimulating factor (G-CSF), alpha-glactosidase A, alpha-L-iduronidase (rhIDU; laronidase), N-acetylgalactosamine-4-sulfatase (rhASB; galsulfase) Tissue plasminogen activator (TPA), Glucocerebrosidase, Interferon (IF) Interferon-beta-1a, Interferon beta-1b, Insulin-like growth factor 1 (IGF-1), somatotropin (ST) and chymosin.

The cells may also be genetically modified to express a polynucleotide—e.g. siRNA sequence or an miRNA sequence.

According to one embodiment, the polynucleotide sequence is a dsRNA.

The polynucleotide sequence may be incorporated into a nucleic acid construct, as further described herein below or may be introduced per se, (i.e. without incorporating into a construct).

To express exogenous a recombinant polypeptide, a polynucleotide sequence encoding the polypeptide is preferably ligated into a nucleic acid construct suitable for mammalian cell expression. Such a nucleic acid construct includes a promoter sequence for directing transcription of the polynucleotide sequence in the cell in a constitutive or inducible manner.

Constitutive promoters suitable for use with some embodiments of the invention are promoter sequences which are active under most environmental conditions and most types of cells such as the cytomegalovirus (CMV) and Rous sarcoma virus (RSV). Inducible promoters suitable for use with some embodiments of the invention include for example the tetracycline-inducible promoter (Zabala M, et al., Cancer Res. 2004, 64(8): 2799-804).

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci.

USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Various methods can be used to introduce the expression vector of some embodiments of the invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6):504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

According to one embodiment, the recombinant protein is modified such that it is covalently attached to a cell penetrating peptide (CPP).

According to still another embodiment, the cells are stem cells (e.g. mesenchymal stem cells, embryonic stem cells, induced pluripotent stem cells) which have been ex vivo differentiated so as to express (preferably secrete) a factor useful for the treatment of a disease.

Ex vivo differentiated can be effected using methods known in the art including by genetic modification and/or culturing in a differentiation medium that comprises growth factors and other factors known to induce differentiation.

Exemplary cells include immune cell, stem cell, progenitor cell, islet cell, bone marrow cells, hematopoietic cells, tumor cells, lymphocytes, leukocytes, granulocytes, hepatocytes, monocytes, macrophages, fibroblasts, neural cells, mesenchymal stem cells, embryonic stem cells, neural stem cells, or other cell with regenerative properties and combinations thereof.

As mentioned hereinabove, the cells of the present invention can be derived from either autologous sources or from allogeneic sources such as human cadavers or donors. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42:29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70:479-83, Chang T M and Prakash S. Procedures for microencapsulation of enzymes, cells and genetically engineered microorganisms. Mol Biotechnol. 2001, 17:249-60, and Lu M Z, et al., A novel cell encapsulation method using photosensitive poly(allylamine alpha-cyanocinnamylidene-acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23:849-56).

Other microcapsules are based on alginate, a marine polysaccharide (Sambanis, A. Encapsulated islets in diabetes treatment. Diabetes Thechnol. Ther. 2003, 5:665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10:6-9; Desai, T. A. Microfabrication technology for pancreatic cell encapsulation. Expert Opin Biol Ther. 2002, 2:633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

The cells of the present invention may be pre-seeded on a scaffold which is subsequently transplanted into the paranasal sinuses or the subarachnoid cavity. Alternatively, the scaffold can be pre-transplanted into the paranasal scaffold or the subarachnoid cavity, following which the cells may be transplanted thereto.

As used herein, the term "scaffold" refers to a 3 dimensional matrix upon which cells may be attached and optionally cultured (i.e., survive and preferably proliferate for a predetermined time period).

Preferably the size of the scaffold is selected such that it does not block the parasinuses. Contemplated size of a scaffold for insertion into the paranasal sinus is about 1 mm (thickness)×2-5 cm (diameter).

The scaffold of the present invention may be made uniformly of a single polymer, co-polymer or blend thereof. However, it is also possible to form a scaffold according to the invention of a plurality of different polymers. There are no particular limitations to the number or arrangement of polymers used in forming the scaffold. Any combination which is biocompatible, may be formed into fibers, and degrades at a suitable rate, may be used. Tissue engineering approaches using injectable, in situ gel forming systems to create scaffold inside PNS may be used.

Both the choice of polymer and the ratio of polymers in a co-polymer may be adjusted to optimize the stiffness of the scaffold. The molecular weight and cross-link density of the scaffold may also be regulated to control both the mechanical properties of the scaffold and the degradation rate (for degradable scaffolds). The mechanical properties may also be optimized to mimic those of the tissue at the implant site. The shape and size of the final scaffold should be adapted for the implant site and tissue type.

Scaffold material may comprise natural or synthetic organic polymers that can be gelled, or polymerized or solidified (e.g., by aggregation, coagulation, hydrophobic interactions, or cross-linking) into a 3-D open-lattice structure that entraps water or other molecules, e.g., to form a hydrogel. Structural scaffold materials may comprise a single polymer or a mixture of two or more polymers in a single composition. Additionally, two or more structural scaffold materials may be co-deposited so as to form a polymeric mixture at the site of deposition. Polymers used in scaffold material compositions may be biocompatible, biodegradable and/or bioerodible and may act as adhesive substrates for cells. In exemplary embodiments, structural scaffold materials are easy to process into complex shapes and have a rigidity and mechanical strength suitable to maintain the desired shape under in vivo conditions.

In certain embodiments, the structural scaffold materials may be non-resorbing or non-biodegradable polymers or materials.

The phrase "non-biodegradable polymer", as used herein, refers to a polymer or polymers which at least substantially (i.e. more than 50%) do not degrade or erode in vivo. The terms "non-biodegradable" and "non-resorbing" are equivalent and are used interchangeably herein.

Such non-resorbing scaffold materials may be used to fabricate materials which are designed for long term or permanent implantation into a host organism. In exemplary embodiments, non-biodegradable structural scaffold materials may be biocompatible. Examples of biocompatible non-biodegradable polymers which are useful as scaffold materials include, but are not limited to, polyethylenes, polyvinyl chlorides, polyamides such as nylons, polyesters, rayons, polypropylenes, polyacrylonitriles, acrylics, polyisoprenes, polybutadienes and polybutadiene-polyisoprene copolymers, neoprenes and nitrile rubbers, polyisobutylenes, olefinic rubbers such as ethylene-propylene rubbers, ethylene-propylene-diene monomer rubbers, and polyurethane elastomers, silicone rubbers, fluoroelastomers and fluorosilicone rubbers, homopolymers and copolymers of vinyl acetates such as ethylene vinyl acetate copolymer, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyvinylpyrrolidones, polyacrylonitrile butadienes, polycarbonates, polyamides, fluoropolymers such as polytetrafluoroethylene and polyvinyl fluoride, polystyrenes, homopolymers and copolymers of styrene acrylonitrile, cellulose acetates, homopolymers and copolymers of acrylonitrile butadiene styrene, polymethylpentenes, polysulfones, polyesters, polyimides, polyisobutylenes, polymethylstyrenes, and other similar compounds known to those skilled in the art.

In other embodiments, the structural scaffold materials may be a "bioerodible" or "biodegradable" polymer or material.

The phrase "biodegradable polymer" as used herein, refers to a polymer or polymers which degrade in vivo, and wherein erosion of the polymer or polymers over time occurs concurrent with or subsequent to release of the islets. The terms "biodegradable" and "bioerodible" are equivalent and are used interchangeably herein.

Such bioerodible or biodegradable scaffold materials may be used to fabricate temporary structures. In exemplary embodiments, biodegradable or bioerodible structural scaffold materials may be biocompatible. Examples of biocompatible biodegradable polymers which are useful as scaffold materials include, but are not limited to, polylactic acid, polyglycolic acid, polycaprolactone, and copolymers thereof, polyesters such as polyglycolides, polyanhydrides, polyacrylates, polyalkyl cyanoacrylates such as n-butyl cyanoacrylate and isopropyl cyanoacrylate, polyacrylamides, polyorthoesters, polyphosphazenes, polypeptides, polyurethanes, polystyrenes, polystyrene sulfonic acid, polystyrene carboxylic acid, polyalkylene oxides, alginates, agaroses, dextrins, dextrans, polyanhydrides, biopolymers such as collagens and elastin, alginates, chitosans, glycosaminoglycans, and mixtures of such polymers. In still other embodiments, a mixture of non-biodegradable and bioerodible and/or biodegradable scaffold materials may be used to form a biomimetic structure of which part is permanent and part is temporary.

PLA, PGA and PLA/PGA copolymers are particularly useful for forming the scaffolds of the present invention. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer. The erosion of the polyester scaffold is related to the molecular weights. The higher molecular weights, weight average molecular weights of 90,000 or higher, result in polymer scaffolds which retain their structural integrity for longer periods of time; while lower molecular weights, weight average molecular weights of 30,000 or less, result in both slower release and shorter scaffold lives. For example, poly(lactide-co-glycolide) (50:50) degrades in about six weeks following implantation.

In an exemplary embodiment, scaffold materials may comprise naturally occurring substances, such as, fibrinogen, fibrin, thrombin, chitosan, collagen, alginate, poly(N-isopropylacrylamide), hyaluronate, albumin, collagen, synthetic polyamino acids, prolamines, polysaccharides such as alginate, heparin, and other naturally occurring biodegradable polymers of sugar units.

In certain embodiments, structural scaffold materials may be ionic hydrogels, for example, ionic polysaccharides, such as alginates or chitosan. Ionic hydrogels may be produced by cross-linking the anionic salt of alginic acid, a carbohydrate polymer isolated from seaweed, with ions, such as calcium cations. The strength of the hydrogel increases with either increasing concentrations of calcium ions or alginate. For example, U.S. Pat. No. 4,352,883 describes the ionic cross-linking of alginate with divalent cations, in water, at room temperature, to form a hydrogel matrix. In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly (acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole). Polyphosphazenes are polymers with backbones consisting of nitrogen and phosphorous atoms separated by alternating single and double bonds. Each phosphorous atom is covalently bonded to two side chains. Polyphosphazenes that can be used have a majority of side chains that are acidic and capable of forming salt bridges with di- or trivalent cations. Examples of acidic side chains are carboxylic acid groups and sulfonic acid groups. Bioerodible polyphosphazenes have at least two differing types of side chains, acidic side groups capable of forming salt bridges with multivalent cations, and side groups that hydrolyze under in vivo conditions, e.g., imidazole groups, amino acid esters, glycerol, and glucosyl. Bioerodible or biodegradable polymers, i.e., polymers that dissolve or degrade within a period that is acceptable in the desired application (usually in vivo therapy), will degrade in less than about five years or in less than about one year, once exposed to a physiological solution of pH 6-8 having a temperature of between about 25° C. and 38° C. Hydrolysis of the side chain results in erosion of the polymer. Examples of hydrolyzing side chains are unsubstituted and substituted imidizoles and amino acid esters in which the side chain is bonded to the phosphorous atom through an amino linkage.

Typically, the scaffolds of the present invention are porous. The porosity of the scaffold may be controlled by a variety of techniques known to those skilled in the art. The minimum pore size and degree of porosity is dictated by the need to provide enough room for the cells and for nutrients to filter through the scaffold to the cells. The maximum pore size and porosity is limited by the ability of the scaffold to maintain its mechanical stability after seeding. As the porosity is increased, use of polymers having a higher modulus, addition of stiffer polymers as a co-polymer or mixture, or an increase in the cross-link density of the polymer may all be used to increase the stability of the scaffold with respect to cellular contraction.

The scaffolds may be made by any of a variety of techniques known to those skilled in the art. Salt-leaching, porogens, solid-liquid phase separation (sometimes termed freeze-drying), and phase inversion fabrication may all be used to produce porous scaffolds. Fiber pulling and weaving (see, e.g. Vacanti, et al., (1988) Journal of Pediatric Surgery, 23:3-9) may be used to produce scaffolds having more aligned polymer threads. Those skilled in the art will recognize that standard polymer processing techniques may be exploited to create polymer scaffolds having a variety of porosities and microstructures.

Scaffold materials are readily available to one of ordinary skill in the art, usually in the form of a solution (suppliers are, for example, BDH, United Kingdom, and Pronova Biomedical Technology a.s. Norway). For a general overview of the selection and preparation of scaffolding materials, see the American National Standards Institute publication No. F2064-00 entitled Standard Guide for Characterization and Testing of Alginates as Starting Materials Intended for Use in Biomedical and Tissue Engineering Medical Products Applications".

Therapeutic compounds or agents that modify cellular activity can also be incorporated (e.g. attached to, coated on, embedded or impregnated) into the scaffold material. Campbell et al (US Patent Application No. 20030125410) which is incorporated by reference as if fully set forth by reference herein, discloses methods for fabrication of 3D scaffolds for stem cell growth, the scaffolds having preformed gradients of therapeutic compounds. The scaffold materials, according to Campbell et al, fall within the category of "bio-inks". Such "bio-inks" are suitable for use with the compositions and methods of the present invention.

Exemplary agents that may be incorporated into the scaffold of the present invention include, but are not limited to those that promote cell adhesion (e.g. fibronectin, integrins), cell colonization, cell proliferation, cell differentiation, cell extravasation and/or cell migration. Thus, for example, the agent may be an amino acid, a small molecule chemical, a peptide, a polypeptide, a protein, a DNA, an RNA, a lipid and/or a proteoglycan.

Proteins that may be incorporated into the scaffolds of the present invention include, but are not limited to extracellular matrix proteins, cell adhesion proteins, growth factors, cytokines, hormones, proteases and protease substrates. Thus, exemplary proteins include vascular endothelial-derived growth factor (VEGF), activin-A, retinoic acid, epidermal growth factor, bone morphogenetic protein, TGFβ, hepatocyte growth factor, platelet-derived growth factor, TGFα, IGF-I and II, hematopoetic growth factors, heparin binding growth factor, peptide growth factors, erythropoietin, interleukins, tumor necrosis factors, interferons, colony stimulating factors, basic and acidic fibroblast growth factors, nerve growth factor (NGF) or muscle morphogenic factor (MMP). The particular growth factor employed should be appropriate to the desired cell activity. The regulatory effects of a large family of growth factors are well known to those skilled in the art.

Since it has been observed that the initial distribution of cells within the scaffold after seeding is related to the cell densities subsequently achieved, methods of cell seeding require careful consideration. Thus, cells can be seeded in a scaffold by static loading, or, more preferably, by seeding in stirred flask bioreactors (scaffold is typically suspended from a solid support), in a rotating wall vessel, or using direct perfusion of the cells in medium in a bioreactor. Highest cell density throughout the scaffold is achieved by the latter (direct perfusion) technique.

The cells may be seeded directly onto the scaffold, or alternatively, the cells may be mixed with a gel which is then absorbed onto the interior and exterior surfaces of the scaffold and which may fill some of the pores of the scaffold. Capillary forces will retain the gel on the scaffold before hardening, or the gel may be allowed to harden on the scaffold to become more self-supporting. Alternatively, the cells may be combined with a cell support substrate in the form of a gel optionally including extracellular matrix components. An exemplary gel is Matrigel™, from Becton-Dickinson. Matrigel™ is a solubilized basement membrane matrix extracted from the EHS mouse tumor (Kleinman, H. K., et al., Biochem. 25:312, 1986). The primary components of the matrix are laminin, collagen I, entactin, and heparan sulfate proteoglycan (perlecan) (Vukicevic, S., et al., Exp. Cell Res. 202:1, 1992). Matrigel™ also contains growth factors, matrix metalloproteinases (MMPs [collagenases]), and other proteinases (plasminogen activators [PAs]) (Mackay, A. R., et al., BioTechniques 15:1048, 1993). The matrix also includes several undefined compounds (Kleinman, H. K., et al., Biochem. 25:312, 1986; McGuire, P. G. and Seeds, N. W., J. Cell. Biochem. 40:215, 1989), but it does not contain any detectable levels of tissue inhibitors of metalloproteinases (TIMPs) (Mackay, A. R., et al., BioTechniques 15:1048, 1993). Alternatively, the gel may be growth-factor reduced Matrigel, produced by removing most of the growth factors from the gel (see Taub, et al., Proc. Natl. Acad. Sci. USA (1990); 87 (10:4002-6). In another embodiment, the gel may be a collagen I gel, alginate, or agar. Such a gel may also include other extracellular matrix components, such as glycosaminoglycans, fibrin, fibronectin, proteoglycans, and glycoproteins. The gel may also include basement membrane components such as collagen IV and laminin. Enzymes such as proteinases and collagenases may be added to the gel, as may cell response modifiers such as growth factors and chemotactic agents.

The cells of the present invention may be transplanted per se, or as part of a pharmaceutical composition.

As used herein a "pharmaceutical composition" refers to a preparation of one or more of the cell populations described herein with other chemical components such as physiologically suitable carriers and excipients. The purpose of the pharmaceutical composition is to facilitate administration of the active ingredients to the subject.

Herein the term "active ingredient" refers to the agents, which increase the amount or activity of the lysosomal enzymes in the brain.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered active ingredients. An adjuvant is included under these phrases.

Herein, the term "excipient" refers to an inert substance added to the pharmaceutical composition to further facilitate administration of an active ingredient of the present invention. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

The pharmaceutical composition may be manufactured by processes well known in the art, e.g., by means of conventional mixing, dissolving, granulating, dragee-making, levigating, emulsifying, encapsulating, entrapping or lyophilizing processes.

The pharmaceutical composition may comprise a proteolytic enzyme inhibitor so as to prevent the hydrolysis of the desired peptide and protein drug (e.g. insulin) in the nasal cavity and, thus, improve the stability of the protein drug at the absorption site. For example, camostatmesilate, an aminopeptidase and trypsin inhibitor, improved the nasal delivery of vasopressin and desmopressin.

Additionally, or alternatively, the pharmaceutical composition may comprise an absorption enhancer. Preferably, the absorption promoter should be rapid-acting, resulting in transient and reversible modulation of the absorptive properties or physiology of the nasal mucosa, and not be absorbed systemically. Further, it should be devoid of any toxic, irritating or allergic activity. The degree of absorption enhancement should be predictable and reproducible. They should also not permit entry of potentially dangerous environmental materials and should be compatible with drugs and adjuvants in the preparation. Examples of compounds that may be used as absorption enhances include saponin, sodium deoxycholate, ethylendiamine tetra-Acetic Acid (EDTA) and lecithin, surfactants, cationic polymers, chitosan and its derivatives, poly-L-arginine, cationized gelatin, cyclodextrin and its derivatives, tight junction modulating lipids, tight junction modulating peptides, nitric oxide donors, N-acetyl-L-cysteine, bile salt and its derivatives, and fatty acid and its derivatives and others from the below list.

1% sodium deoxycholate, 1% sodium taurodihydrofusidate (STDHF), 0.5% lysophosphatidylcholine (LPC), 0.125% dodecylmaltoside, 0.5% Laureth-9, 0.5% sucrose cocoate, 3.5% soybean-derived sterol, 1.0% sterol glucoside, Cyclodextrins (5% DM-bCD, 5% DM-bCD, 30% DM-bCD 2, DM-bCD, 5% DM-bCD, 5% a-CD); Cell-penetrating peptides (0.5 mM L-R8, 0.5 mM D-R8, 0.5 mM D-penetratin, 0.5 mM L-penetratin, 0.5 mM shuffle (R,K fix)); Cationized polymers (0.5% chitosan, 85.7% chitosan, 0.2% sperminated gelatin, 0.2% aminated H-gelatin, 0.4% aminated H-gelatin, 0.2% aminated H-gelatin, 0.2% aminated L-gelatin) and Chelators (e.g. 0.5% EDTA-2Na).

Further information on absorption enhancers may be found in Duan et al., Drug Discovery Today, Volume 15, Numbers 11/12, June 2010, incorporated herein by reference.

The present invention further contemplates using different methods to achieve mucoadhesion, thereby enhancing bioavailability.

Bioadhesive microsphere delivery system: To avoid rapid clearance owing to ciliary beating and prolong the residence time in the nasal mucosa, the present invention contemplates the use of crosslinked dextran microsphere, starch microsphere, aminated gelatin microspheres or hyaluronic acid ester microspheres. Other types of bioadhesive microsphere delivery systems such as biadhesive powders are disclosed in Duan et al., Drug Discovery Today, Volume 15, Numbers 11/12, June 2010, incorporated herein by reference.

The pharmaceutical composition should contain the active ingredients in an amount effective to achieve disease treatment.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. Following this, a dose can be formulated in animal models (e.g. streptozotocin STZ rats) to achieve a desired plasma concentration or titer. To find a minimal dose of pancreatic islets required for diabetes reversal, aliquots of 500, 1000, 1500 and 2000 islets may initially be implanted in diabetic rats. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredients which are sufficient to achieve the desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of the composition to be administered will be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Transplantation of the cells into the nose, and more specifically to the paranasal sinuses (e.g. the maxillary sinus) may be effected in a non-invasive manner by inserting a flexible (e.g. malleable) tube which enters the ostium which is localized under the median nasal concha. Preferably, when inserted into the nose, the end of the tube reaches the paranasal sinus cavity, prior to allowing release of the cells.

Thus, according to another aspect of the present invention there is provided an endoscopic device comprising a container attached to a flexible tubing wherein the inner surface of the container is coated with an agent that prevents adhesiveness of cell aggregates thereto.

The device generally includes a tubing, e.g., a catheter, attached to a container having an elongate pusher at its end. The tubing may be flexible or rigid, or may be designed to have varying degrees of stiffness along its length, e.g., the distal portion of the tubing may be stiffer than the proximal portion. In addition, the distal portion of the tubing may be variously angulated to facilitate positioning and advancement of the conduit through the sinus ostium. For example, the distal portion may be angulated from about 0 degree to about 175 degree, from about 0 degree to about 135 degree, or from about 0 degree to about 90 degree.

The diameter of the lumen of the tubing is typically between about 200-1000 µm or 100-500 µm and the tubing is typically about 5-20 cm in length. The tubing may be made from any biocompatible material including, but not limited to, stainless steel and any of its alloys; titanium alloys, e.g., nickel-titanium alloys; polymers, e.g., polyethylene and copolymers thereof, polyethylene terephthalate or copolymers thereof, nylon, silicone, polyurethanes, fluoropolymers, poly(vinylchloride), and combinations thereof, depending on the amount of flexibility or stiffness desired. The pusher and container may be made from similar materials.

The tubing is attached to a container for holding the cells. The container is coated on its inner surface with an agent that prevents cell aggregates from sticking thereto. The surface of the pusher which contacts the cells may be coated with a similar agent. Such agents include, but are not limited to silicon and polyethylene. Once access through a sinus ostium has been obtained with the tubing, the pusher slidably engages the cells and is advanced until the cells exit the container and advance through the tubing into the sinus. An optic fiber may also be used while positioning the tubing to aid with visualization of the ostium. The optic fiber may be incorporated into the device of the present invention or may be used separately (e.g. by using an endoscope).

In certain cases, e.g., when ostia are closed or difficult to access, cell transplantation into one or more sinuses may be completed through the sinus wall using a sharp-tipped conduit, e.g., a needle, trocar, or angiocatheter, with or without visualization using computer image-guided technology or endoscopy. Once the appropriate access point for the sinus has been determined, force is applied to the sharp-tipped conduit so that it punctures the sinus wall. Advancement of a pusher through container then deposits the cells into the sinus.

FIG. 4 shows an exemplary transplantation device 10. The device includes a population of cells 12, a tubing 14 having a lumen 16, wherein the tubing 14 is attached to a container 18 into which is inserted a pusher 20. The pusher 20 may further comprise a handle 24 for easy grasp. The inside walls of the container 18 are coated with an agent which prevents sticking of cellular material. The device may further incorporate an optic fiber 22 for visualization. The pusher 20 is advanced distally within the container 18 to slidably engage the cells 20 and move it up the container 18 through the tubing 14 into the sinus. Although the tip of the tubing is shown to be blunt in FIG. 4, it may also be sharp and/or beveled, usually depending on the implant delivery method.

A force applied to the pusher 20 allows a predetermined amount of cells 12 into the tubing 14, e.g., by contact with a pusher or pressurized gas, could be used to deliver the cells 12 into the sinus.

As mentioned, the device described herein may incorporate, or may be used in conjunction with, endoscopes. Such endoscopes will typically include light transmitting optical fibers for casting light in the area to be viewed by the scope and image transmitting optical fibers for carrying an image received by the scope to an eyepiece or monitor device located outside the patient's body. In some embodiments a scope, such as a disposable and/or flexible scope, may be affixed to the working device. Examples of such endoscopes that are suitable for incorporation into the working devices of this invention include that described in U.S. Pat. Nos. 4,708,434; 4,919,112; 5,127,393; 5,519,532; 5,171,233, 5,549,542, 6,551,239 and 6,572,538 as well as published United States Patent Application No. 2001/0029317A1, the entireties of which are expressly incorporated herein by reference.

Alternatively, transplantation into the paranasal sinuses may be effected using a minimally invasive method whereby a needle is used to enter the sinus via a thin bone under the lower concha.

A more invasive means of carrying out the transplantation is by performing a small cut in the upper gum of the mouth and introducing a needle through the bone into the paranasal sinus. Another example is to use an opening in the upper tooth for cell transplantation into the maxillary sinus.

Transplantation into the subarachnoid cavity may be effected by methods and devices for cell delivery in CNS such as described by Potts M B, Silvestrini M T, Lim D A. Devices for cell transplantation into the central nervous system: Design considerations and emerging technologies. Surg Neurol Int. 2013 Mar. 19; 4 (Suppl 1):S22-30. doi: 10.4103/2152-7806.109190).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, New York (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Transplantation of Insulin-Producing Beta Cell Line (Ins-1) into PNS of Diabetic Rats Materials and Methods Inbred Lewis rats (males, 270-280 g) were used as recipient for insulinoma cell (INS-1) transplantation. Insulin dependent diabetes was induced by iv injection of streptozotocin (STZ) at 85 mg/kg body weight. This dose of STZ results in a stable and spontaneously irreversible diabetes in Lewis rats. Rats were pretreated with 10 mg/kg cyclosporine A (CyA) 2 days before transplantation followed by a daily dosage of CyA. One week after STZ injection, about $30 \times 10^6$ INS-1 cells were transplanted (Tx) into the PNS of diabetic rats.

Due to the relatively small rat PNS volume, noninvasive cell delivery into the rat PNS is complicated. (The total volume of rat PNS is ~50 mm3 compared to a very large human PNS occupying ~60-80 cm3 space). Thus, a simple surgical procedure was used and recipient animals were anesthetized with ketamine/xylozine, followed by a 0.5-cm longitudinal incision of skin between the eyes. The plate of the bone was then exposed and trepanized with a 1 mm burr in the direction of the PNS. An aliquot of cells (~5 µl) was introduced into the PNS using a pipette tip.

Head and pancreas were removed for immunohistochemical analysis two weeks after cell implantation as described previously (Bloch K, et al., Acta Biomater. 2010; 6(3):1200-5; Bloch K, et al., Histochem Cell Biol. 2012; 137(6):801-10).

Results

Reverse of diabetes was shown after transplantation of insulin-producing beta cell line (INS-1) into PNS of STZ-diabetic Lewis rats treated with cyclosporine A (CyA) (FIG. 2). Immunohistochemical analysis indicates insulin staining of INS-1 cells (brown color) localized in PNS after two-week post-transplantation period (FIGS. 3A-B). Immunostaining of blood vessel endothelial cells with vWF shows intensive neovascularization of grafted tissue (Data not shown).

Example 2

Islet Transplantation in a Subarachnoid Cavity Surrounding Olfactory Bulb of Diabetic Rats In this example, the present inventors studied the different parameters of glucose homeostasis and islet morphology following islet transplantation in a subarachnoid cavity of diabetic rats. This transplantation procedure enabled the assembly of grafted islets directly onto the glomeruli of the olfactory bulb.

Materials and Methods

Chemicals:

The CMRL and RPMI 1640 culture media, Hanks balanced saline solution (HBSS), fetal calf serum (FCS), penicillin, streptomycin, and other reagents for tissue culture were obtained from Biological Industries (Beit Haemek, Israel); Collagenase NB8 from Serva (Heidelberg, Germany); Bovine serum albumin (BSA), bovine DNAse, streptozotocin (STZ) and histopaque were acquired from Sigma-Aldrich (St Louis, Mo., USA); Dithizone (DTZ) was obtained from Merck (Darmstadt, Germany). Rat C-peptide ELISA kit was purchased from Mercodia AB (Uppsala, Sweden), the primary guinea pig anti-insulin from Progen GmbH (Heidelberg, Germany), mouse anti-glucagon antibodies from Sigma (St Louis, Mo., USA), Antibody diluent and fluorescent mounting medium were purchased from Dako (Carpinteria, Calif., USA). Secondary goat anti-rabbit, anti-mouse and anti-guinea pig antibodies ($Cy^{tm2}$ and $Cy^{tm3}$) and peroxidase-conjugated goat anti-rabbit Ig were purchased from Jackson Immuno Research Laboratories Inc. (Baltimore, Pa., USA). Adhesion microscopic slides were from Marieneld GmbH & Co. KG-(Lauda-Konigshofen, Germany).

Animals and Diabetes Induction:

10-12-week-old male Lewis inbred rats (Harlan, Jerusalem, Israel) weighing 260-280 g, were used in all experiments. All procedures were approved by the Institutional Animal Care and Use Committee. Diabetes was induced by a single intravenous injection of 85 mg STZ/kg body weight. STZ was injected after being dissolved in citrate buffer (pH 4.5). Only animals with persistent hyperglycemia (>350 mg/dl) were used as transplant recipients.

Pancreatic Islet Isolation and Dithizone (DTZ) Staining:

Islets were isolated from pancreata of Lewis rats by enzymatic digestion with collagenase solution containing 12 PZ units/ml collagenase NB8 and 1 mg/mL bovine DNAse in HBSS solution for 15 min at 37° C. Islets were purified using a discontinuous Histopaque gradient density and collected from the 1.077 interphase. The islets were then washed and cultured in 8 ml CMRL:RPMI medium 1640 (1:1) supplemented with 10% FCS and 1% antibiotics, overnight in a $CO_2$ incubator (5% $CO_2$/95% air) before being transplanted. Islet quantity was expressed as the number of IEQ, which is calculated based on the number and diameter of the DTZ-stained islets in four aliquots of 150 ul from islet suspension using the standard IEQ conversion factors. The number of IEQ obtained per pancreas varied from 500 to 600.

The morphology of isolated islets was analyzed after DTZ-staining using an inverted microscope. DTZ stock solution was prepared by dissolving 50 mg of DTZ in 5 ml of dimethyl sulfoxide. For in vitro staining, 10 µl of DTZ-stock solution was dissolved in 1 ml of phenol red free RPMI medium 1640. Culture medium was replaced by DTZ solution. The staining procedure was performed at 37° C. for 15 minutes in a $CO_2$-incubator. Islets stained with DTZ were washed twice with fresh phenol red free RPMI medium 1640, analyzed by an inverted microscope and images were captured.

Islet Transplantation Procedure:

Animals were anesthetized using ketamine and xylazine (100 mg and 15 mg per kg body weight, respectively). Throughout surgery, the eyes were covered with ointment to prevent drying out and infection of the cornea. After head fur shaving and disinfection, the skin overlying the skull was incised using a scalpel, the soft tissue and muscles were removed from the surface of the frontal skull. Using a stainless steel burr disinfected in 70% ethanol, a hole of 1 mm diameter was then made in the frontal bone 2 mm lateral to the midline at the location shown in FIG. 7A. The dura mater and the arachnoid membrane were then perforated and a polyethylene cannula containing 3000 IEQ resuspended in 20 µl of HBSS was inserted into the subarachnoid space. Following islet introduction into the subarachnoid cavity by air pressure, the hole was sealed using bone wax and the incision was closed with surgical suture. Histological analysis revealed localization of grafted islets directly onto the glomeruli of the olfactory bulb (FIG. 5C and FIG. 7B).

Metabolic Follow-Up:

Non-fasting blood glucose concentration was measured between 9.00 am and 10.00 am in whole blood with a portable glucometer (Acu-Check; Hoffmann La Roche, Basel Switzerland). An intraperitoneal test tolerance to glucose (IPTTG) was performed in all experimental groups. For IPTTG, 25% dextrose solution was injected intraperitoneally following 6 h fast at a dose of 4 µl/g body weight. Blood glucose was measured before and at 15, 30, 60 and 120 min post-glucose injection. Body weight was measured weekly before and after STZ injection. C-peptide level was tested in blood serum using an ELISA kit for rat C-peptide, according to manufacturer protocol (Mercodia AB, Sweden).

Histological Evaluation of Transplanted Islets and Pancreas:

For histological analysis, the recipients were sacrificed 2 months following transplantation. Pancreata and heads were fixed in 10% buffered formalin and processed routinely for histology. Heads were placed in Calci-clear rapid (Life Science Products, Inc. Frederick, Colo., USA) to decalcify the bones before embedding in paraffin. Histological sections (4 µm thick) were stained with H&E. Immunohistochemical analysis of islet hormone expression and vascularization was performed as described previously [Bloch K, et al., Histochem Cell Biol 2012; 137:801; Bloch K, et al., Acta Biomater 2010; 6:1200). Briefly, each section was blocked with 20% normal serum and incubated with primary polyclonal guinea pig anti-insulin antibodies (1:1000) and monoclonal mouse anti-glucagon antibodies (1:2000) overnight, at 4° C. After washing, sections were incubated with secondary antibodies: peroxidase-conjugated goat anti-guinea pig Ig (1:400), $Cy^{tm3}$-conjugated affinipure anti-guinea pig Ig (1:400) and anti-mouse $Cy^{tm2}$ (1:400) for one hour at room temperature. For horseradish peroxidase (HRP) staining, 3% $H_2O_2$ was used to block endogenous peroxidase activity. All dilutions were made with Dako antibody diluent.

Immunochemistry Controls and Analysis:

Immunostaining of insulin and glucagon was negative when the primary antibodies were replaced with Dako antibody diluent or normal serum. The cells were analyzed by light and fluorescent microscopy (BX-52, Olympus Ltd, Japan); images were captured by digital camera and merged using Image-Pro plus v. 5.1.

Statistical Analysis:

Data are expressed as mean±SD of repeated experiments. Student's t test (two-tailed) was used to evaluate the statistical significance of differences between groups.

Results

Figure 5A:
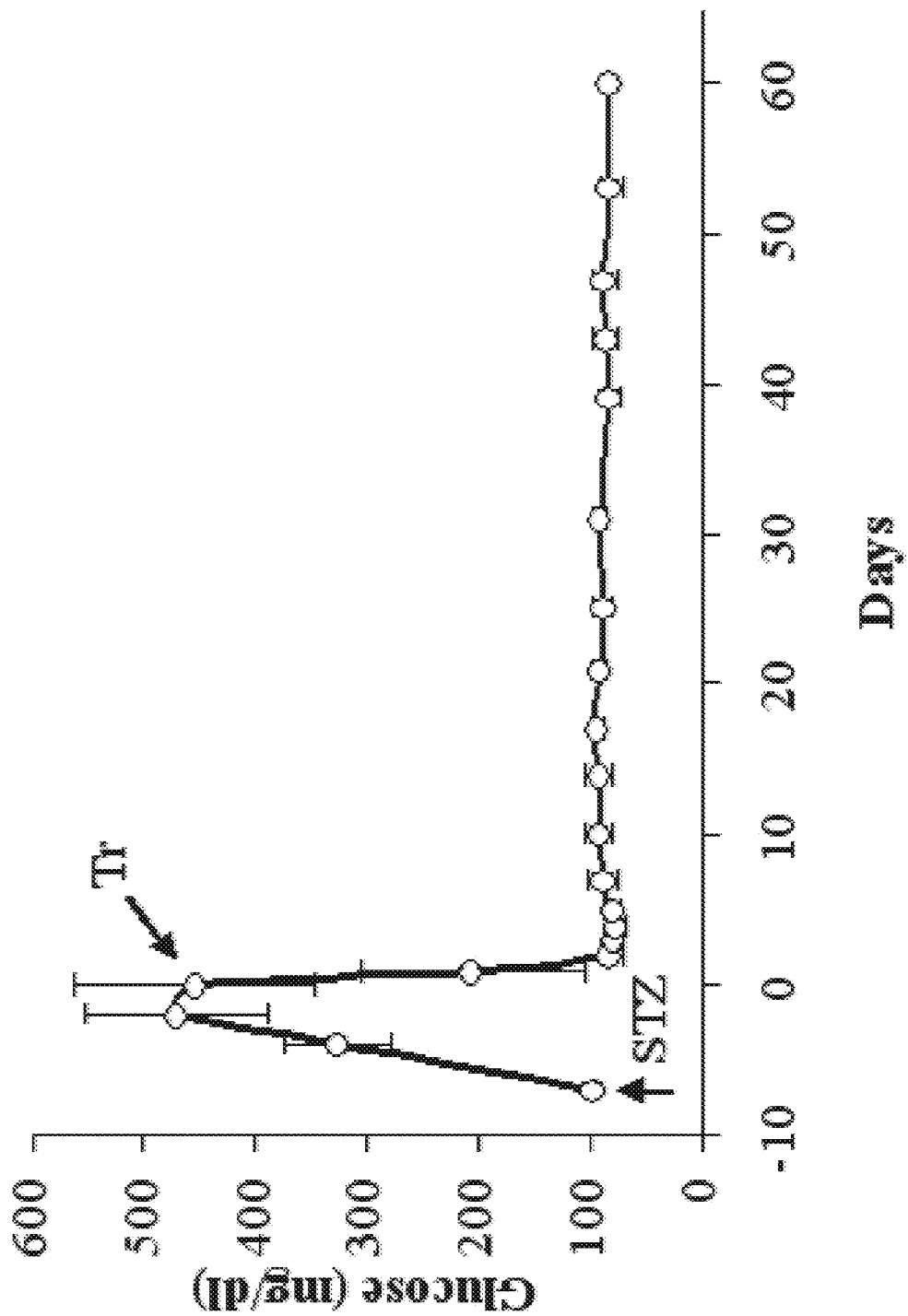

As shown in FIG. 5A, all severely diabetic rats transplanted with 3000 islet equivalents achieved normoglycemia within the first two days which was maintained for two months post transplantation. One month and two months after transplantation the rats demonstrated normal glucose tolerance typical for healthy animals (FIG. 5B). These data correlate well with the normalization of blood C-peptide level found in transplanted animals (526±90, 56±47 and 372±129 pmol/L in intact, diabetic and transplanted rats, respectively). In contrast, the non-transplanted diabetic animals were permanently hyperglycemic, showing impaired glucose tolerance, decreased level of blood C-peptide and body weight loss. They died within the first month after diabetes induction.

Figure 5D:
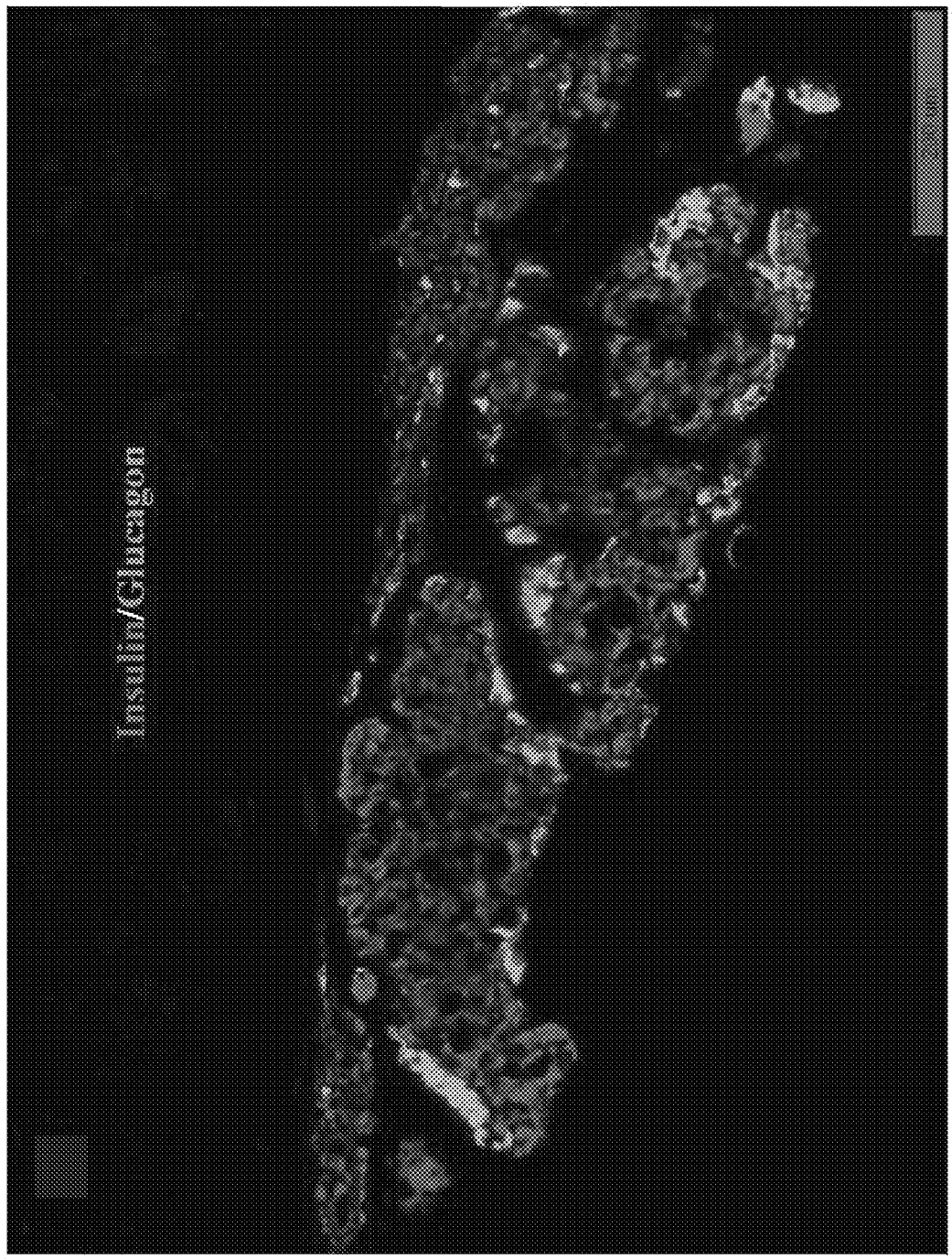

Two months following transplantation, rat heads were fixated in formalin, decalcified and processed routinely for histology. Hematoxylin and eosin staining demonstrated the intact morphology of transplanted pancreatic islets located in the subarachnoid cavity between the frontal bone of skull and the olfactory bulb. Microscopic examination of histological sections stained for insulin revealed the localization of islet grafts directly on the glomerular layer of the olfactory bulb (FIG. 5C). In contrast to the intact pancreas, where individual islets are separated one from another by multilayer exocrine tissue, the islets transplanted on the surface of the olfactory bulb formed an islet-like tissue, where individual islets joined one another. In order to compare islet cellular architecture in the intact pancreas and following transplantation in a subarachnoid cavity, double staining for insulin and glucagon was performed. The arrangement of beta and alpha cells in the grafted islets was typical for rodents: the insulin producing beta cells were found in the central area of islets, while glucagon producing alpha cells had a mantle position (FIG. 5D). Thus, the islet transplantation directly onto the glomeruli of the olfactory bulb resulted in a preservation of islet architecture and a quick reversal of hyperglycemia to stable normoglycemia.

Additional advantages of this transplantation procedure may be possible effects of transplanted islets on improvement of cognitive function. The central nervous system is known to be very sensitive to disrupted insulin signaling and glucose homeostasis which occur in diabetic patients. In this regard, we suggest that transplantation of pancreatic islets in the subarachnoid cavity surrounding the olfactory bulb can not only serve to reverse diabetes, but also to provide adequate insulin supply to brain, restore cerebral glucose homeostasis and cognitive functions. A schematic presentation of possible anti-diabetic and anti-dementia effects of islets transplanted in subarachnoid cavity is shown in FIG. 6.

In conclusion, the achievement of long-term islet graft function in subarachnoid cavity surrounding the olfactory bulb of diabetic rats provides an opportunity to clarify the effects of insulin and other islet hormones secreted inside blood brain barrier on diabetes and to estimate the impact of transplanted islets on various neurodegenerative and neuropsychological disorders.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a cognitive disorder in a subject in need thereof, comprising transplanting a therapeutically effective amount of pancreatic beta cells into the subarachnoid cavity, wherein said transplanting into said subarachnoid cavity is performed between the frontal bone of the skull and the olfactory bulb of the subject, thereby treating the cognitive disorder.

2. The method of claim 1, wherein said cognitive disorder is selected from the group consisting of Stroke, Schizophrenia, Parkinson's, Epilepsy, ALS, Drug and alcohol addiction, Alzheimer's and Huntington's disease.

3. The method of claim 1, wherein said pancreatic beta cells are in an aggregated state, wherein said aggregates are greater than 50 microns in diameter.

4. The method of claim 1, wherein said transplanting into said subarachnoid cavity is performed such that at least 20% of said pancreatic beta cells localize to the olfactory bulb of the subject.

5. The method of claim 1, wherein said pancreatic beta cells are seeded on a scaffold prior to the transplanting.

6. The method of claim 1, wherein said pancreatic beta cells comprise immunoisolated cells.

7. A method of treating a cognitive disorder in a subject in need thereof, comprising transplanting a therapeutically effective amount of pancreatic beta cells into the subarachnoid cavity of the subject, thereby treating the cognitive disorder.

8. The method of claim 7, wherein said cognitive disorder is selected from the group consisting of Stroke, Schizophrenia, Parkinson's, Epilepsy, ALS, Drug and alcohol addiction, Alzheimer's and Huntington's disease.

9. The method of claim 7, wherein said pancreatic beta cells are in an aggregated state, wherein said aggregates are greater than 50 microns in diameter.

10. The method of claim 7, wherein said pancreatic beta cells are seeded on a scaffold prior to the transplanting.

11. The method of claim 7, wherein said pancreatic beta cells comprise immunoisolated cells.

* * * * *